United States Patent [19]

Hyoguchi et al.

[11] Patent Number: 5,467,655
[45] Date of Patent: Nov. 21, 1995

[54] METHOD FOR MEASURING PROPERTIES OF COLD ROLLED THIN STEEL SHEET AND APPARATUS THEREFOR

[75] Inventors: Takao Hyoguchi; Katsuhiro Kawashima, both of Sagamihara, Japan

[73] Assignee: Nippon Steel Corporation, Tokyo, Japan

[21] Appl. No.: 419,968

[22] Filed: Apr. 10, 1995

Related U.S. Application Data

[63] Continuation of Ser. No. 858,103, Mar. 26, 1992, abandoned.

[30] Foreign Application Priority Data

Mar. 27, 1991 [JP] Japan ..................... 3-063142

[51] Int. Cl.$^6$ ............... G01N 29/12; G01H 11/04; G01H 13/00
[52] U.S. Cl. ............... 73/579; 73/630; 73/643
[58] Field of Search ............... 73/630, 643, 579, 73/597, 598

[56] References Cited

U.S. PATENT DOCUMENTS

| 3,592,051 | 7/1971 | Kubo ............................. 73/570 |
| 4,164,873 | 8/1979 | Böttcher et al. ............... 73/643 |
| 4,218,924 | 8/1980 | Fortunko et al. ............... 73/643 |

FOREIGN PATENT DOCUMENTS

| 1-83322 | 3/1989 | Japan . |
| 1-214757 | 8/1989 | Japan . |
| 2-210258 | 8/1990 | Japan . |

OTHER PUBLICATIONS

Ultrasonic Testing of Materials by Josef Krautkrämer and Herbert Krautkrämer, 2nd Edition, (1977) chapter 11 pp. 265–286.

Primary Examiner—Hezron E. Williams
Assistant Examiner—Rose M. Finley
Attorney, Agent, or Firm—Kenyon & Kenyon

[57] ABSTRACT

A method for measuring properties of a cold rolled thin steel sheet, comprising the determination, by using a resonant electromagnetic ultrasonic wave sensor for a standing wave, of the ratio of a thickness resonant frequency of a transverse ultrasonic wave propagating within a cold rolled thin steel sheet in the direction of thickness while polarized in a direction parallel to the direction of rolling to a thickness resonant frequency of a longitudinal ultrasonic wave propagating within the cold rolled thin steel sheet in the direction of thickness, and the ratio of a resonant frequency of a transverse ultrasonic wave propagating within the cold rolled thin steel sheet in the direction of thickness while polarized in a direction normal to the direction of rolling to a thickness resonant frequency of a longitudinal ultrasonic wave propagating in the direction of thickness, and approximately determining the Young's modulus and the Lankford value according to a computing formula using the resultant two measured -ratio values, the sound speed ratio of a SH0 plate wave regarded as a constant value and a known value of modulus of elasticity; and an apparatus for measuring properties of a cold rolled thin steel sheet comprising an electromagnetic ultrasonic wave device, a computing device and a controlling device for executing the measurement of properties and the computation.

5 Claims, 8 Drawing Sheets

METHOD FOR MEASURING PROPERTIES OF COLD ROLLED THIN STEEL SHEET AND APPARATUS THEREFOR

This application is a continuation of application Ser. No. 07/858 103 filed Mar. 26 1992, now abandoned.

BACKGROUND OF THE INVENTION

1. Field of the Invention

The present invention relates to a method and apparatus for rapidly and non-destructively measuring properties of a cold rolled thin steel sheet in an off-line system, or a method and apparatus for conducting a non-destructive measurement during execution of the step of passing through a sheet in an on-line system.

2. Description of Related Art

A cold rolled thin steel sheet is required to have a high press-formability because it is used for a body of an automobile or in domestic electrical appliances. The cold rolled thin steel sheet is a polycrystalline material, and the press-formability thereof is determined almost by the so-called "aggregate structure".

The press-formability has hitherto been estimated by an X-ray pole figure method or a Lankford value (an r value). The X-ray pole figure method is time consuming, however, since a test piece should be cut out from a cold rolled thin steel sheet and irradiated with an X-ray for a measurement. Further, in this method, since a test piece is cut out purposely, 30 the test method is destructive, and therefore is unsuitable, particularly for an on-line measurement. On the other hand, the method wherein a Lankford value is measured is time consuming, since an accurate measurement on a change in the size of a tensile test piece is necessary. Further, in this method, since a test piece is cut out from the cold rolled thin steel sheet, the measuring method is destructive. In another method, a simple method is proposed (C. A. Stickers and Mould, "The use of Young's modulus for predicting the plastic strain ratio of low carbon steel sheets", Metallurgical Transaction, Vol. 1, pp. 1303–1312 (1970)). Utilizing an empirical correlation between the Young's value measured by a natural polarization method and the Lankford value, but since a test piece is cut out from a cold rolled thin steel sheet, this measuring method is also destructive.

For this reason, a method wherein the velocity of an ultrasonic wave is measured has been proposed wherein a non-destructive measurement is conducted through the use of a cold rolled thin steel sheet per se without cutting out a test piece as in the above-described measuring method. In a method wherein the Young's modulus or Lankford value of a cold rolled thin steel sheet is obtained by the above-described non-destructive measuring method (for example, see Japanese Unexamined Patent Publication (Kokai) No. 2-210258), the above-described $K_1$ and $K_2$ values are measured by means of a resonant electromagnetic ultrasonic wave sensor and, at the same time, the ratio, $K_3$, of the speed of SH0 sheet wave ultrasonic wave, $V_{SH0}$ (45°), propagating within the cold rolled thin steel sheet in a direction at 45° to the direction of rolling to the speed of SH0 plate wave ultrasonic wave, $V_{SH0}$ (0°) or $V_{SH0}$ (90°), propagating in a direction parallel to or normal to the direction of rolling should be measured by means of a SH0 plate wave ultrasonic wave sensor of an electromagnetic ultrasonic wave sensor system. That is, it is necessary to use an resonant electromagnetic ultrasonic wave sensor and a SH0 sheet wave ultrasonic wave sensor. In particular, two pairs of the above-described resonant electromagnetic ultrasonic wave sensors and SH0 plate wave ultrasonic wave sensors should be used as an ultrasonic wave sensor for measuring the $K_3$ value. Therefore, in this case, there occur problems in that it is difficult to reduce the size of the measuring apparatus and it is difficult to stably generate and detect a plate wave ultrasonic wave when a non-contact measurement is conducted in an on-line system. The term "SH (shear horizontal) plate wave" used herein is intended to mean a transverse wave that is parallel (horizontal) to the boundary surface of a thin steel sheet or the like and causes a particle to be polarized in a direction orthogonal to the direction of advance. The above-described SH0 wave is one of the SH plate waves and is intended to mean a 0 (zero) mode wave.

In a patent directed to an apparatus for evaluating a drawability of a metallic thin sheet (for example, Japanese Unexamined Patent Publication (Kokai) No. 1-214757), a $S_0$ mode ultrasonic wave is propagated in directions of 0°, 450° and 90° in the direction of rolling, and the Lankford value is obtained by measuring the time taken for the ultrasonic wave to propagate a given distance. The drawability is also referred to as a press-formability, which is an important factor in a metallic thin sheet, for example, a body of an automobile. Usually, the drawability is estimated on the basis of Lankford values. In this method, however, three pairs of electromagnetic ultrasonic wave sensors for transmission and an electromagnetic ultrasonic wave sensor for receiving are necessary, so that the size of the whole measuring apparatus is large, that is, 30 cm×30 cm or more, and therefore is not very convenient.

In other patents (for example, Japanese Unexamined Patent Publication (Kokai) No. 64-83322), the velocities of three types of ultrasonic waves are measured, and the ratio, K, of the average velocity of two transverse waves to the velocity of a longitudinal wave is calculated. This patent demonstrates that the K value is related to the coefficient of crystal orientation, $W_{400}$, and the in-plane average value of Lankford values. In effect, after a secondary regression formula of the K value and the in-plane average value of the Lankford value is determined from an empirical formula, the in-plane average value of the Lankford value is estimated from the above-described K value. In this method, however, since use is made of the ratio of the velocity of a longitudinal wave to the average velocity of sound of two transverse waves, the number of data is only one. Further, since the coefficients of crystal orientation, that is, $W_{420}$ and $W_{440}$, are not taken into consideration, it is believed that the precision of the calculation is lowered. Further, according to working examples of the above-described patent, a metallic thin sheet is brought into contact with an ultrasonic wave probe to conduct the measurement, which renders the above-described method unsuitable for a measurement in an on-line system.

SUMMARY OF THE INVENTION

An object of the present invention is to provide a method of determining the in-plane average value of Young's modulus or the in-plane average value of a Lankford value of a cold rolled thin steel sheet from measurements of the resonant frequency ratios, $K_1$ and $K_2$, and three moduli of elasticity of a single crystal of iron with a view to solving the above-described problems associated with a high-precision measurement in a non-destructive and non-contact manner in an on-line system, and a measuring apparatus therefor.

In order to attain the above-described object, the present invention provides a method for measuring properties of a cold rolled thin steel sheet including the following steps. Specifically, the method according to the present invention comprises the steps of:

determining the ratio of a thickness resonant frequency of a transverse ultrasonic wave propagating within a cold rolled thin steel sheet in the direction of thickness while polarized in a direction parallel to the direction of rolling to a thickness resonant frequency of a longitudinal ultrasonic wave propagating within the cold rolled thin steel sheet in the direction of thickness, and the ratio of a resonant frequency of a transverse ultrasonic wave propagating within the cold rolled thin steel sheet in the direction of thickness while polarized in a direction normal to the direction of rolling to a thickness resonant frequency of a longitudinal ultrasonic wave propagating in the direction of thickness;

regarding as a constant value without measurement the ratio of the velocity of a SH0 plate wave propagating within said cold rolled steel sheet in a direction 45° to the direction of rolling to the velocity of sound of a SH0 sheet wave propagating in a direction parallel to or normal to the direction of rolling; and approximately computing the in-plane average value of Young's moduli and the in-plane average value of Lankford values of the cold rolled thin steel sheet from said three ratios and a known modulus of elasticity of a single crystal of iron.

Further, according to the present invention, there is provided an apparatus for measuring properties of a cold rolled thin steel sheet, comprising an electromagnetic ultrasonic wave device including at least a resonant electromagnetic ultrasonic wave sensor for generating and detecting said two transverse ultrasonic waves and said one longitudinal ultrasonic wave; a computing device for computing the Young's modulus and the Lankford value of the cold rolled thin steel sheet based on said ratio of the thickness resonant frequency measured by said electromagnetic ultrasonic wave device; and a controlling mechanism for maintaining a constant gap between the resonant electromagnetic ultrasonic wave sensor and the cold rolled steel sheet.

In a preferred embodiment of the present invention, the electromagnetic ultrasonic wave device comprises a coil for conducting a high frequency current and for inducing an eddy current in the cold rolled thin steel sheet; a magnet for applying a predetermined magnetic field in the cold rolled thin steel sheet; and said resonant ultrasonic wave sensor for detecting said two transverse ultrasonic waves and said one longitudinal ultrasonic wave generated in the vicinity of the surface of the cold rolled thin steel sheet owing to interaction between the eddy current and the magnetic field.

In this case, it is preferable to obtain the three thickness resonant frequencies by a method wherein the transverse ultrasonic wave and longitudinal ultrasonic wave are generated and detected while sweeping the frequency of a high frequency current flowing in said coil and the frequency at which the detected ultrasonic wave becomes maximum is recorded.

More specifically, the ratio of a thickness resonant frequency of a transverse ultrasonic wave propagating within the cold rolled thin steel sheet in the direction of thickness while polarized in a direction parallel to the direction of rolling to a thickness resonant frequency of a longitudinal ultrasonic wave propagating in the direction of thickness, and the ratio of a thickness resonant frequency of a transverse ultrasonic wave propagating within the cold rolled thin steel sheet in the direction of thickness while polarized in a direction normal to the direction of rolling to a thickness resonant frequency of a longitudinal ultrasonic wave propagating in the direction of thickness, are measured by means of a resonant electromagnetic ultrasonic wave sensor alone, and the in-plane average value of the Young's modulus and the in-plane average value of the Lankford value are determined according to an approximate computation expression.

BRIEF DESCRIPTION OF DRAWINGS

The above-described objects and features according to the present invention will become apparent from the following successive descriptions of working examples with reference to the accompanying drawings.

DESCRIPTION OF THE PREFERRED EMBODIMENTS

Theoretical support related to the present invention will now be described prior to the description of embodiments of the present invention.

At the outset, a method for calculating the in-plane average value of Young's moduli by using the $K_1$, $K_2$ and $K_3$ values will be described according to Japanese Unexamined Patent Publication (Kokai) No. 2-210258 or literature (Katsuhiro Kawashima, "Nondestructive characterization of texture and plastic strain ratio of metal sheets with electromagnetic acoustic transducers", J. Acoust. Soc. America, Vol. 87, No. 2, February 1990, pp. 681–690), and the method of the present invention wherein the in-plane average value of Young's moduli is approximately determined by using the measured values of $K_1$ and $K_2$ alone will then be described.

At the outset, the theoretical support will be described according to the above-described patent. Although the cold rolled thin steel sheet is a polycrystal comprising many fine single crystals of iron (cubic crystals), it can be regarded as a continuum having an anisotropy from the macroscopic viewpoint. The thin steel sheet regarded as a continuum is approximately considered to have physical properties of plane symmetry with respect to three planes orthogonal to each other (1. a rolling plane (xy plane), 2. a plane perpendicular to the rolling plane and parallel to the direction of rolling (xz plane), and 3. a plane perpendicular to the rolling plane and perpendicular to the direction of rolling (yz plane)). x shows the direction of rolling and corresponds to a longitudinal direction of the thin steel sheet. y shows a direction normal to x and corresponds to the direction of the width of the thin steel sheet. z shows a direction perpendicular to both x and y and corresponds to a direction perpendicular to the plane of the thin steel sheet. In such a case, it is known that the matrix of modulus of elasticity of the thin steel sheet has nine different moduli of elasticity and can be expressed as follows.

$$\begin{bmatrix} C_{11} & C_{12} & C_{13} & 0 & 0 & 0 \\ C_{12} & C_{22} & C_{23} & 0 & 0 & 0 \\ C_{31} & C_{23} & C_{33} & 0 & 0 & 0 \\ 0 & 0 & 0 & C_{44} & 0 & 0 \\ 0 & 0 & 0 & 0 & C_{55} & 0 \\ 0 & 0 & 0 & 0 & 0 & C_{66} \end{bmatrix} \quad (1)$$

wherein $C_{ij}$ represents nine different moduli of elasticity. On the other hand, it is known that the proportion of a single crystal having a given orientation $(\theta, \phi, \emptyset)$ to the thin steel sheet among many single crystals constituting the polycrystal can be expressed by a crystal orientation distribution function $W(\xi, \phi, \emptyset)$ (hereinafter referred to as "CODF") (see R. J. Roe, "Description of crystallite orientation in polycrystalline materials", Journal of Applied Physics, Vol. 36, pp. 2024–2031(1965)), wherein $\xi = \cos\theta$.

It is also known that $W(\xi, \phi, \emptyset)$ can be expressed by series expansion using a generalized Legendre's function, $Z_{lmn}$.

$$W(\xi, \phi, \emptyset) = \sum_{l=0}^{\infty} \sum_{m=-1}^{1} \sum_{n=-1}^{1} W_{lmn} Z_{lmn} \exp(-im\phi)\exp(-in\emptyset) \quad (2)$$

wherein $\emptyset$, $\phi$ and $\emptyset$ are an Euler's angle used for expressing the relationship between the single crystal and the thin steel sheet. $\xi$ is $\cos\theta$. $W(\xi, \phi, \emptyset)$ is a function that represents the proportion of the amount of a single crystal having a given orientation $(\theta, \phi, \emptyset)$ to the thin steel sheet, and is called a "crystal orientation distribution function". $W_{lmn}$ is a CODF coefficient. In $W_{lmn}$, $W_{400}$, $W_{420}$ and $W_{440}$ are known to relate to elastic properties of a polycrystal.

As described above, it is known that the cold rolled thin steel sheet has nine different moduli of elasticity, $C_{ij}$, which can be expressed by the following formulae using six independent variables, that is, three moduli of elasticity, $C^0_{11}$, $C^0_{12}$ and $C^0_{44}$, and three CODF coefficients, that is, $W_{400}$, $W_{420}$ and $W_{440}$, with respect to a single crystal of iron (see C. M. Sayers, "Ultrasonic velocities in anisotropic polycrystalline aggregates" Journal of Physics, D15, pp 2157–2167 (1982)).

$$C_{11} = C^0_{11} - 2C^0 \left\{ \frac{1}{5} - \frac{6}{35} \sqrt{2\pi^2} \left[ W_{400} - \frac{2}{3}(10)^{1/2} W_{240} + \frac{1}{3}(70)^{1/2} W_{440} \right] \right\}$$

$$C_{22} = C^0_{11} - 2C^0 \left\{ \frac{1}{5} - \frac{6}{35} \sqrt{2\pi^2} \left[ W_{400} + \frac{2}{3}(10)^{1/2} W_{420} + \frac{1}{3}(70)^{1/2} W_{440} \right] \right\}$$

$$C_{33} = C^0_{11} - 2C^0 \left\{ \frac{1}{5} - \frac{16}{35} \sqrt{2\pi^2} W_{400} \right\}$$

$$C_{44} = C^0_{44} + C^0 \left\{ \frac{1}{5} - \frac{16}{35} \sqrt{2\pi^2} [W_{400} + (5/2)^{1/2} W_{420}] \right\} \quad (3)$$

$$C_{55} = C^0_{44} + C^0 \left\{ \frac{1}{5} + \frac{4}{35} \sqrt{2\pi^2} [W_{400} + (70)^{1/2} W_{420}] \right\}$$

$$C_{66} = C^0_{44} + C^0 \left\{ \frac{1}{5} + \frac{4}{35} \sqrt{2\pi^2} [W_{400} + (70)^{1/2} W_{440}] \right\}$$

$$C_{23} = C^0_{12} + C^0 \left\{ \frac{1}{5} - \frac{16}{35} \sqrt{2\pi^2} [W_{400} + (5/2)^{1/2} W_{420}] \right\}$$

$$C_{31} = C^0_{12} + C^0 \left\{ \frac{1}{5} - \frac{16}{35} \sqrt{2\pi^2} [W_{400} - (5/2)^{1/2} W_{420}] \right\}$$

$$C_{12} = C^0_{12} + C^0 \left\{ \frac{1}{5} + \frac{4}{35} \sqrt{2\pi^2} [W_{400} - (70)^{1/2} W_{440}] \right\}$$

wherein $C^0 = C^0_{11} - C^0_{12} - 2C^0_{44}$.

In this connection, the CODF coefficients, $W_{400}$, $W_{420}$ and $W_{440}$, are respectively expressed by the following formulae (4), (5) and (6).

$$W_{400} = F_1(C^0_{11}/C^0, C^0_{44}/C^0, K_1^2, K_2^2) = \frac{35}{16\sqrt{2\pi^2}} \left[ \frac{1}{5} + \frac{C^0_{44}}{C^0} - \left( \frac{C^0_{11}}{2C^0} + \frac{C^0_{44}}{C^0} \right) \left( \frac{K_1^2 + K_2^2}{K_1^2 + K_2^2 + 1} \right) \right] \quad (4)$$

$$W_{420} = F_2(C^{011}/C^0, C^{044}/C^0, K_1^2, K_2^2) = \frac{35}{16(5)^{1/2}\pi^2} \left( \frac{C^0_{11}}{2C^0} + \frac{C^0_{44}}{C^0} \right) \left( \frac{K_1^2 - K_2^2}{K_1^2 + K_2^2 + 1} \right) \quad (5)$$

$$W_{440} = F_3(C^{011}/C^0, C^{012}/C^0, C^{044}/C^0, K_1^2, K_2^2, K_3^2) = \frac{(35)^{1/2}}{16\pi^2 K_3} \left\{ \frac{C^0_{11}}{2C^0} - \frac{C^0_{12}}{2C^0} - \frac{3}{10} \left( \frac{C^0_{44}}{C^0} + \frac{1}{5} \right) (2K_3 - 1) - \quad (6)$$

-continued $$\frac{8\sqrt{2}\pi^2(K_3-1)}{35} F_1(C_{11}^0/C^0, C_{44}^0/C^0, K_1^2, K_2^2) -$$

$$\frac{256\pi^4 [F_2(C_{11}^0/C^0, C_{44}^0/C^0, K_1^2, K_2^2)]^2}{245\left[C_{11}^0/C^0 - 2/5 + \left(\frac{32}{35}\right)\sqrt{2}\pi^2 F_1(C_{11}^0/C^0, C_{44}^0/C^0, K_1^2, K_2^2)\right]}$$

Figure 1:
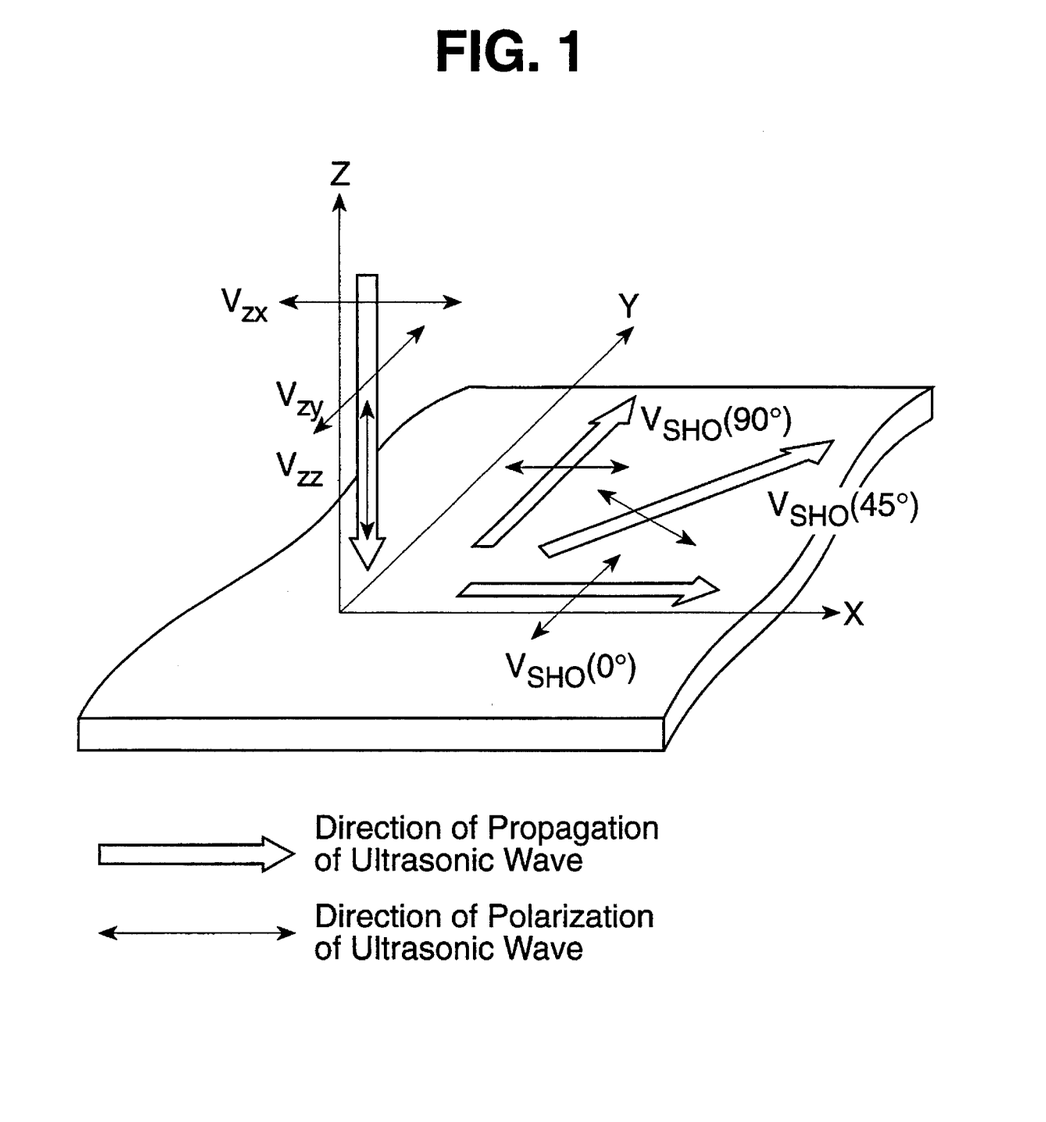
FIG. 1 is a diagram showing the direction of propagation and the direction of polarization of ultrasonic waves of various modes related to the present invention.

An ultrasonic wave of various modes related to the present invention is shown in FIG. 1. In FIG. 1, a thick arrow represents the direction of propagation of an ultrasonic wave, and a thin arrow represents the direction of oscillation of an ultrasonic wave. Although these arrows are drawn outside the thin steel sheet for convenience, it is a matter of course that all of the actual ultrasonic waves propagate within the thin steel sheet. Vzz represents the velocity of a longitudinal wave propagating in the direction of sheet thickness; Vzx represents the velocity of a transverse wave deviating in the direction of rolling and propagating in the direction of sheet thickness and Vzy represents the velocity of a transverse wave deviating in a direction normal to the direction of rolling and propagating in the direction of sheet thickness. $V_{SH0}$ (0°) represents the velocity of a SH0 mode plate wave deviating in a direction normal to the direction of rolling and propagating in the direction of rolling; $V_{SH0}$ (90°) represents the velocity of a SH0 mode plate wave deviating in the direction of rolling and propagating within the rolling plane in a direction normal to the direction of rolling, and $V_{SH0}$ (45°) represents the velocity of a SH0 mode plate wave propagating within the rolling plane in a direction 45° to the direction of rolling.

The resonant frequency ratios, that is, $K_1$ and $K_2$, and the velocity ratio, $K_3$, can be determined through the utilization of the formulae (7) and (8) and the formula (9), respectively.

$$f_{zzl} = \frac{l}{2d} V_{zz}, f_{zym} = \frac{m}{2d} V_{zy}, f_{zxn} = \frac{n}{2d} V_{zx} \quad (7)$$

$$K_1 = \frac{lf_{zym}}{mf_{zzl}}, K_2 = \frac{lf_{zxn}}{nf_{zzl}} \quad (8)$$

$$K_3 = \frac{V_{SH0}(45°)}{V_{SH0}(0°)} = \frac{V_{SH0}(45°)}{V_{SH0}(90°)} = \frac{t_0}{t_{45}} \quad (9)$$

wherein $f_{zym}$, $f_{zxn}$ and $f_{zzl}$ represent an m-order resonant frequency of a transversal ultrasonic wave propagating within a cold rolled thin steel sheet in the direction of thickness and polarized in a direction normal to the direction of rolling, an n-order resonant frequency of a transversal ultrasonic wave polarized in a direction parallel to the direction of rolling and a l-order resonant frequency of a longitudinal ultrasonic wave polarized in the direction of thickness.

The velocity in the case that the direction of advance of a SH0 plate wave is in agreement with the direction of rolling is $V_{SH0}$ (0°); the velocity in the case that the direction of advance of the SH0 plate wave is 45° to the direction of rolling is $V_{SH0}$ (45°), and $t_0$ and $t_{45}$ represent respective times taken for the SH0 plate waves advancing at 0° and 45° to the direction of rolling to propagate an identical distance.

The formulae (4) and (5) are already known (see, for example, C. M. Sayers and D. R. Allen, "The influence of stress on the principal polarization directions of ultrasonic shear waves in textured steel plates", Journal of Physics, D17, pp. 1399–1413 (1984)). On the other hand, the formula (6) was found for the first time in Japanese Unexamined Patent Publication (Kokai) No. 2-210258. According to the formulae (4), (5) and (6), the utilization of three known values of modulus of elasticity ($C^0_{11}$=237 GPa, $C^0_{12}$=141 GPa, and $C^0_{44}$=116 GPa) of a single crystal enables all the $W_{400}$, $W_{420}$ and $W_{440}$ values to be obtained by calculation through mere determination of the resonant frequency ratios, $K_1$ and $K_2$, and the velocity ratio, $K_3$. Once the $W_{400}$, $W_{420}$ and $W_{440}$ values are obtained, the substitution of these values for the formula (3) provides nine moduli of elasticity, $C_{ij}$, of the thin steel sheet.

It is well known that the Young's modulus, $E(\alpha)$, of the thin steel sheet within the rolling plane in a direction at an angle of $\alpha$ to the direction of rolling can be expressed by the following formula (see, for example, F. Boric and G. A. Alers, "Measurement of the elastic properties of rolled sheet", Trans. Metal. Soc. AIME 233, 7–11 (1965)).

$$1/E(\alpha) = S_{22} \sin^4 \alpha + S_{11} \cos^4 \alpha + (S_{66} + 2S_{12}) \sin^2 \alpha \cos^2 \alpha \quad (10)$$

wherein $S_{11} = (C_{22}C_{33} - C_{23}^2)S$, $S_{22} = (C_{11}C_{33} - C_{31}^2)S$, $S_{12} = (C_{31}C_{23} - C_{12}C_{33})S$, $S_{66} = 1/C_{66}$, and $S = 1/(C_{11}C_{22}C_{33} + 2C_{12}C_{23}C_{31} - C_{11}C_{23}^2 - C_{33}C_{12}^2)$ The Young's modulus $E(\alpha)$ can be obtained by substituting nine moduli of elasticity, $C_{ij}$, of the thin steel sheet obtained by the above-described method for the formula (10). The average value of Young's moduli within the rolling plane can be determined by the following formula (11).

$$E = [E(0°) + 2E(45°) + E(90°)]/4 \quad (11)$$

A method proposed by the present invention wherein the in-plane average value of Young's moduli can be approximately calculated from the measured values of $K_1$ and $K_2$ and the velocity ratio regarded as a constant value, $K_3$, and three moduli of elasticity of a single crystal of iron.

As is apparent from the formulae (3), (4), (5), (6), (10) and (11), the Young's modulus represented by making use of $K_1$, $K_2$ and $K_3$ can be expressed by making use of parameters $K_p$, $K_M$ and $K_3$ of the formula (12).

$$K_P = \frac{K_1^2 + K_2^2}{K_1^2 + K_2^2 + 1} \quad (12)$$

$$K_M = \frac{K_1^2 - K_2^2}{K_1^2 + K_2^2 + 1}$$

Figure 3:
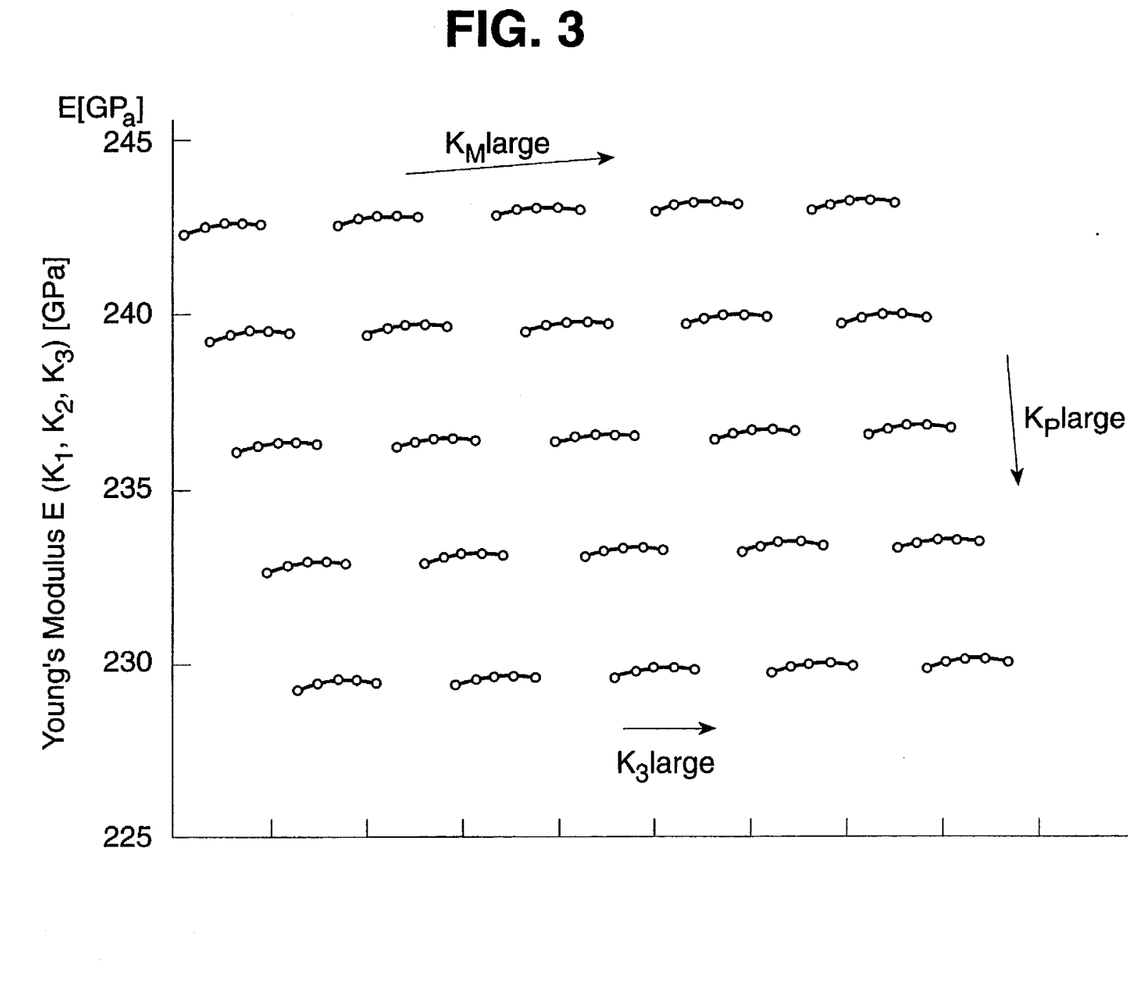
FIG. 3 is a diagram showing the relationship between the change of $K_3$ and the in-plane average value of Young's moduli.
Figure 4:
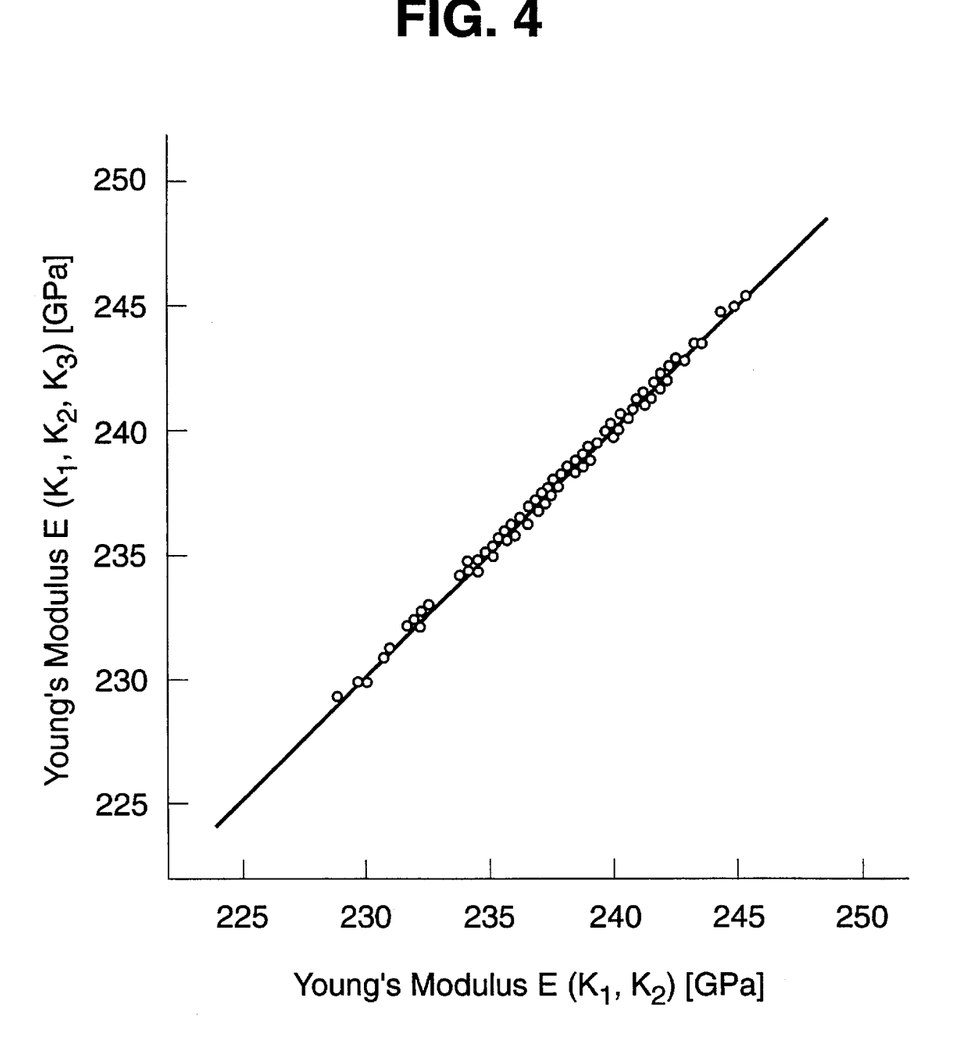
FIG. 4 is a diagram for comparing the in-plane average value of Young's moduli approximately determined from the measured values of resonant frequency ratios, $K_1$ and $K_2$, and the ratio of sound, $K_3=0.96$, according to the present invention, with the in-plane average value of Young's moduli determined from the resonant frequency ratios, $K_1$ and $K_2$, and the ratio of sound, $K_3$.

As a result of measurement of 500 sheets of cold rolled thin sheets, $K_p$, $K_M$ and $K_3$ values were 0.32 to 0.37, −0.4 to 0.0 and 0.940 to 1.024, respectively. The results of simulation, wherein a combination of parameters $K_p$, $K_M$ and $K_3$ respectively in 5 points at equal intervals and a combination of 125 points in total, are substituted for the above-described formulae (3) to (12) are shown in FIG. 3. As is apparent from the results, although the in-plane average value of Young's moduli is a function of three variables, $K_1$, $K_2$ and $K_3$, or $K_p$, $K_M$ and $K_3$, the contribution of $K_3$ is so small that the change in the in-plane average value of Young's modulus with respect to the $K_p$, $K_M$ and $K_3$ values in the above-described respective ranges is as small as about 0.2 GPa. Therefore, when $K_3$ is 0.96, the error of Young's modulus is as small as ±0.2 GPa, and 0.09% or less with respect to a Young's modulus of 240 GPa. Thus, the in-plane average value of Young's moduli can be approximately calculated through the use of $K_p$ and $K_M$, that is, $K_1$ and $K_2$ alone. A strong correlation between the in-plane average value of Young's moduli approximated by using the measured values of $K_1$ and $K_2$ and $K_3$=0.96 and the in-plane average value closely calculated from $K_1$, $K_2$ and $K_3$ is shown in FIG. 4. The in-plane average value of Lankford values can be obtained using these results and by the secondary formula approximation of an empirical relationship between the Young's modulus and the Lankford value using the least square method.

A method of measuring the resonant frequency ratios, $K_1$ and $K_2$, will now be described.

Figure 2A:
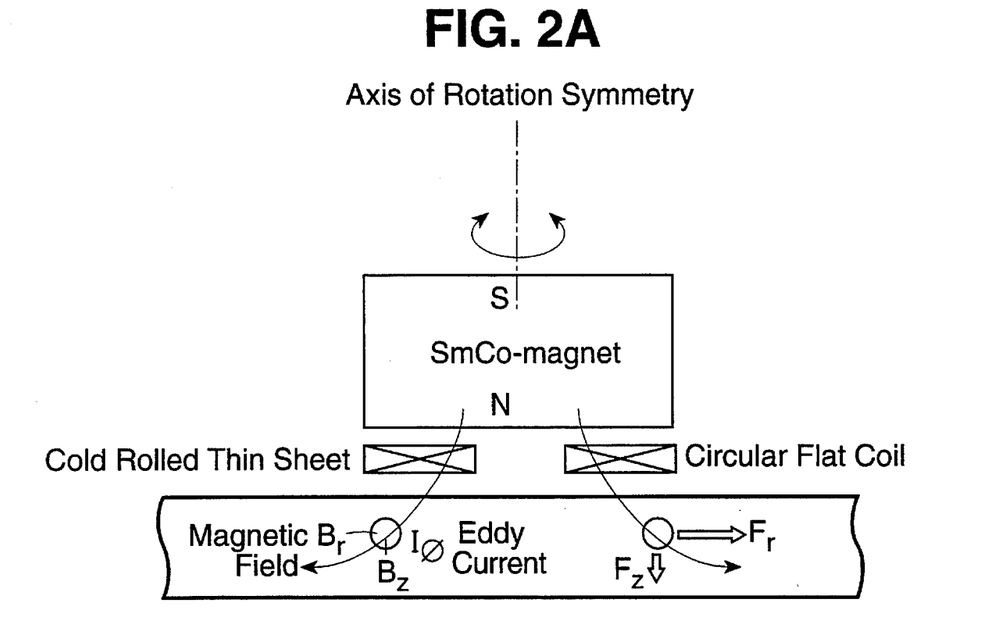
FIG. 2 is a diagram showing a resonant electromagnetic ultrasonic wave sensor for generating and detecting a longitudinal ultrasonic wave and two transverse ultrasonic waves.
Figure 2B:
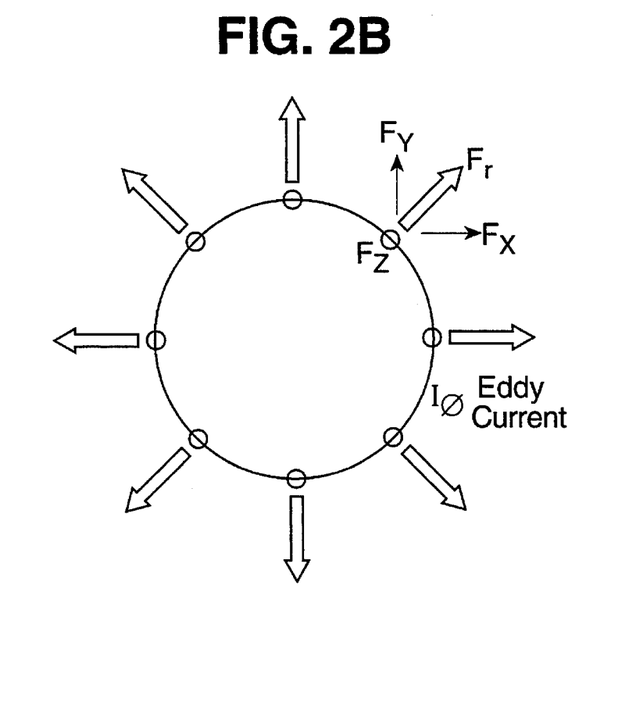

It is known that a standing wave method wherein use is made of an electromagnetic ultrasonic wave (also known as "thickness resonance method"; hereinafter referred to as "resonance method") is suitable for measuring thickness resonant frequencies, $f_{zz}$, $f_{zx}$ and $f_{zy}$, of an ultrasonic wave propagating within a thin steel sheet having a thickness of 2 mm or less in the direction of thickness (see, for example, S. A. Filimonov, B. A. Budenkov, and N. A. Glukhov, "Ultrasonic contactless resonance testing method", Soviet Journal of Nondestructive Testing, No. 1, pp. 102–104 (1971)). An electromagnetic ultrasonic wave sensor used for the resonance method is shown in FIG. 2. FIG. 2 (a) is a front cross-sectional view of the electromagnetic ultrasonic wave sensor. This electromagnetic ultrasonic wave sensor has a symmetrical rotational structure. FIG. 2 (b) is a top view of the electromagnetic ultrasonic wave sensor that shows an eddy current, an electromagnetic force, etc. When a high frequency current flows in a flat circular coil shown in FIG. 2 (a), an eddy current, Iø, is induced in the thin steel sheet. High frequency current means that the current has a frequency which is sufficient to induce an eddy current by which measurable ultrasonic waves can be generated in a thin steel sheet. A magnetic field occurs in the thin steel sheet by means of a permanent magnet. The magnetic field has a component, Bz, perpendicular to the surface of the thin steel sheet and a component, Br, distributed in a parallel and radial manner on the surface of the thin steel sheet. An electromagnetic force, Fr, distributed in a parallel and radial manner in the vicinity of the surface of the thin steel sheet occurs through interaction between Iø and Bz. A perpendicular electromagnetic force, Fz, occurs in the vicinity of the surface of the thin steel sheet through interaction between Iø and Br. The electromagnetic force, Fr, can be divided into a component Fx parallel to the direction of rolling and a component Fy perpendicular to the direction of rolling. Fz causes a longitudinal wave Vzz, propagating in the direction of sheet thickness, to be generated. Fx causes a transverse wave Vzx, deviating in the direction of rolling and propagating in the direction of sheet thickness, to be generated, and Fy causes a transverse wave Vzy, deviating in a direction normal to the direction of rolling and propagating in the direction of sheet thickness, to be generated. The permanent magnet is used for the purpose of generating a magnetic field in the thin steel sheet, and an electromagnet may be used instead of the permanent magnet.

Thus, the generated ultrasonic wave is detected by a reverse physical process. It is known that when the frequency of a high frequency current flowing in a coil satisfies a requirement represented by the formula f=nV/(2d) (wherein V represents velocity, d represents a sheet thickness and n represents an integer), a standing wave occurs within the thin steel sheet in the direction of thickness thereof. The frequency represented by this formula can be obtained by generating and detecting an ultrasonic wave according to the above-described process while sweeping the frequency of a high frequency current flowing in said coil and recording a frequency at which the detected ultrasonic wave becomes maximum. According to the formulae (7) and (8), since the calculation of the resonant frequency ratio is sufficient for this purpose, it is unnecessary to measure the thickness, d, of the thin steel sheet. In order to measure the thickness, d, of a wide thin steel sheet, it is necessary to conduct a measurement by means of an X-ray or the like, so that the elimination of this measurement is advantageous from a practical point of view.

Finally, a method, wherein the resonant frequency ratios, $K_1$ and $K_2$, of the cold rolled thin steel sheet during passing of the steel sheet are measured in an on-line system to determine the in-plane average value of Young's moduli or the in-plane average value of Lankford value, will be described. In order to measure two n-order resonant frequencies of a traverse ultrasonic wave and one (n/2)-order resonant frequency of a longitudinal ultrasonic wave using the resonant electromagnetic ultrasonic wave sensor, a measuring frequency band is set from the nominal sheet thickness and approximate values of three ultrasonic wave speeds, and the frequency is swept by this frequency band, thus enabling the above-described three resonant frequencies to be measured and the $K_1$ and $K_2$ values to be measured. Since the measurement can be conducted in 0.01 sec or less, it can be assumed that the thin steel sheet that travels during this time has a constant material property and a constant sheet thickness, so that the in-plane average value of Young's moduli or the in-plane average value of Lankford value can be obtained.

Figure 5:
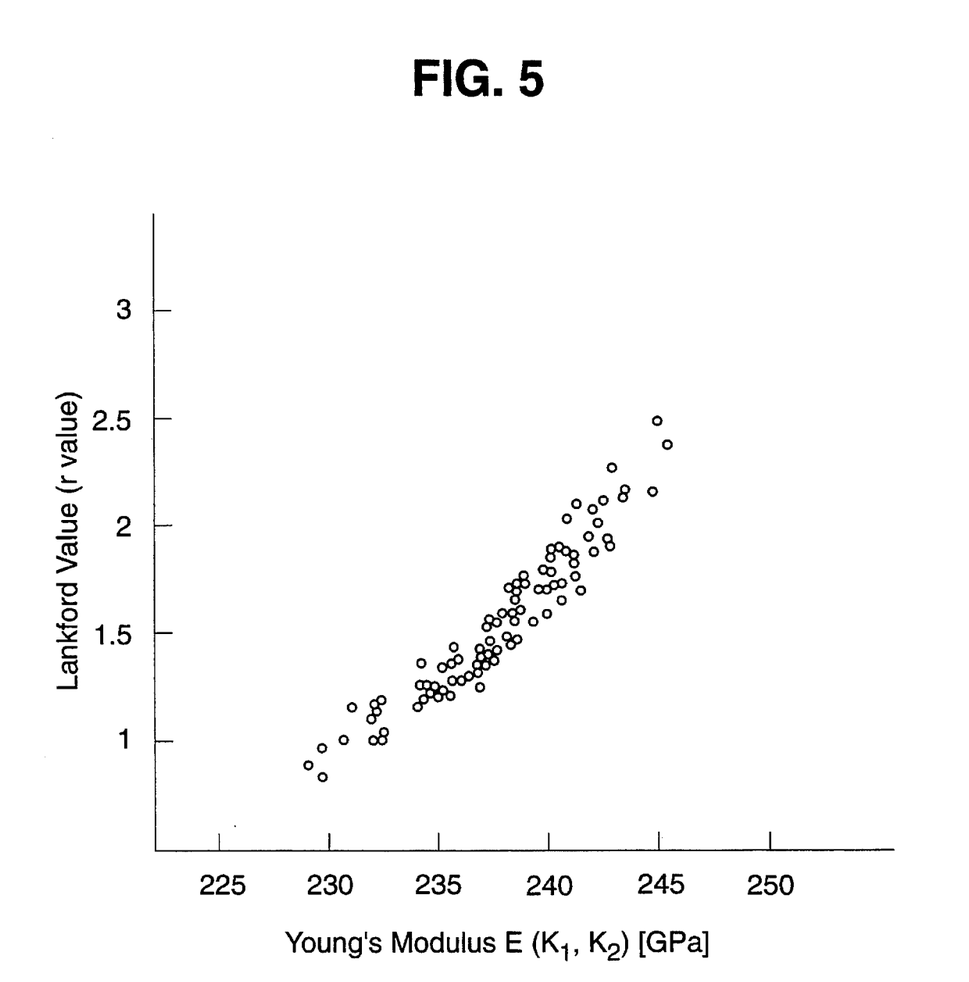
FIG. 5 is a diagram showing the relationship between the in-rolling-plane average value (E) of Young's moduli determined according to the method of the present invention and the in-rolling-plane average value (r) of Lankford values determined by means of a tensile tester.
Figure 6:
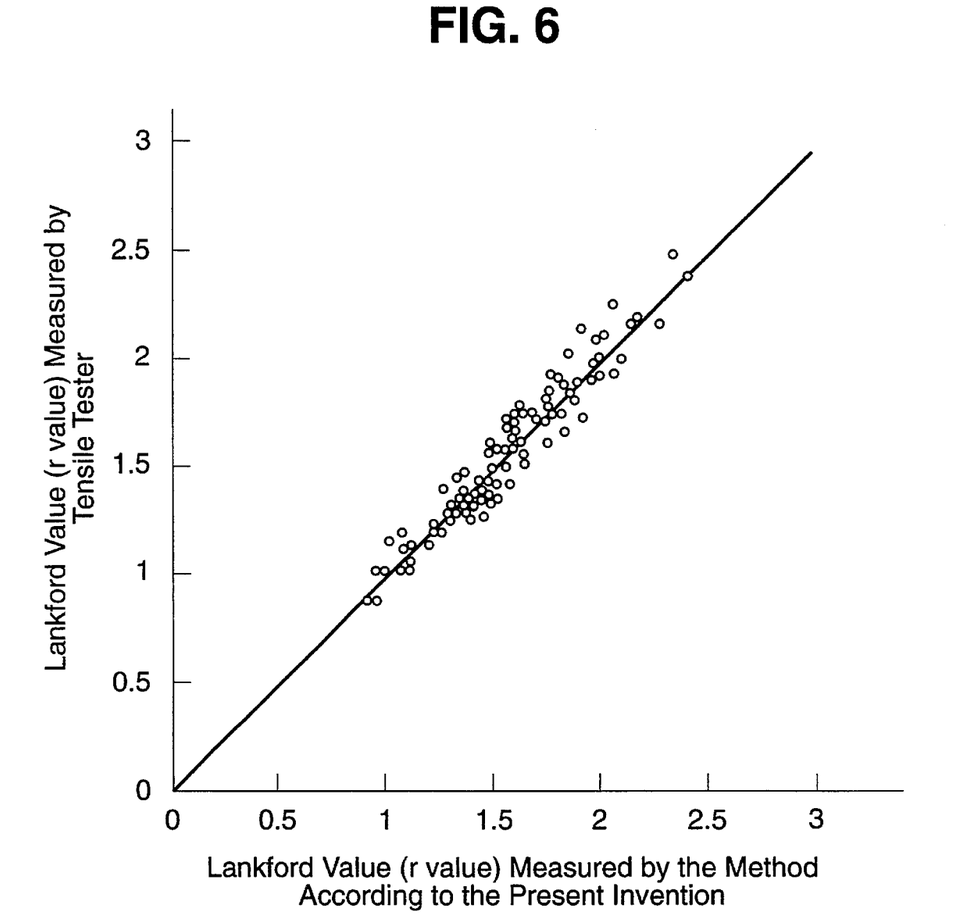
FIG. 6 is a diagram showing the relationship between the in-rolling-plane average value (r) of Lankford values determined according to the method of the present invention and the in-rolling-plane average value (r) of Lankford values determined by means of a tensile tester.

FIGS. 4 to 6 are diagrams showing the relationship between the Young's modulus and Lankford value of cold rolled thin steel sheet produced according to the present invention and the measured value thereof.

More specifically, 100 sheets of thin steel sheets were actually subjected to a measurement of $K_1$ and $K_2$ by means of a resonant electromagnetic ultrasonic wave sensor; the in-plane average value of Young's modulus was approximately determined by taking $K_3$ as 0.96, and the results were compared with the in-plane average value of Young's moduli closely determined through the measurement of $K_1$, $K_2$ and $K_3$ by a method described in Japanese Unexamined Patent Publication (Kokai) No. 2-10258. The results are shown in FIG. 4. The relationship between the in-rolling-plane average value (=[E(0°)+2E(45°)+E(90°)]/4) of Young's moduli of 100 sheets of a thin steel sheet measured by the approximation method according to the present invention and the in-rolling-plane average value (=[r(0°)+2r(45°)+r(90°)]/4) of the Lankford value (r value) of 100 sheets of a thin steel sheet measured by a tensile test is shown in FIG. 5. When the relationship between the Young's modulus and the Lankford value is subjected to a secondary formula approximation by the least squares method, the residual standard deviation becomes about 0.1, thus enabling the in-rolling-plane average value of Lankford values to be determined. The comparison of the Lankford value (r) determined by the method of the present invention with the Lankford value determined by a tensile test is shown in FIG. 6. The Young's modulus and Lankford value approximately determined by the present invention are substantially in agreement with the measured values, which demonstrates that the method of measuring properties of a cold rolled thin sheet according to the present invention is effective.

Figure 7:
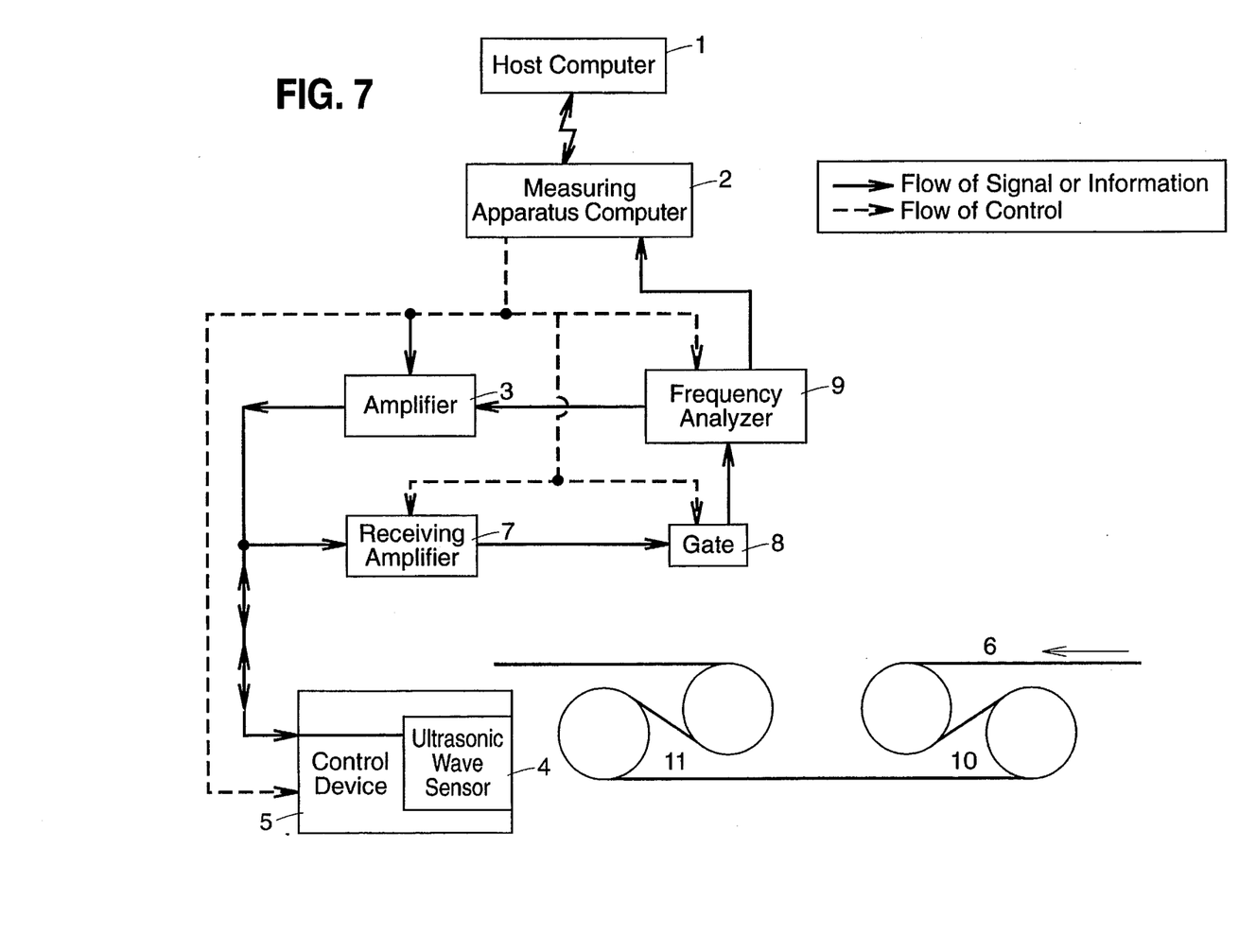
FIG. 7 is a schematic diagram showing a measuring system for obtaining the in-plane average value of Young's moduli or the in-plane average value of Lankford values in an on-line system.

FIG. 7 is a perspective view of a preferred embodiment of an apparatus for measuring properties of a cold rolled thin steel sheet according to the present invention. More specifically, FIG. 7 schematically shows a measuring system wherein the above-described $K_1$ and $K_2$ values are measured in an on-line system to determine the in-plane average value of Young's moduli or the in-plane average value of Lankford values. Numeral 1 designates a host computer that transmits and receives steel sheet information of a cold rolled thin steel sheet (for example, steel sheet number, sheet thickness, sheet passing rate, etc.) and the results of a measurement. Numeral 2 designates a computer for the measuring apparatus, numeral 3 a transmitting amplifier, numeral 4 a resonant electromagnetic ultrasonic wave sensor, numeral 5 a controlling device, numeral 6 a cold rolled thin steel sheet, numeral 7 a receiving amplifier, numeral 8 a gate, numeral 9 a frequency analyzer, numeral 10 an input bridle roll, and numeral 11 an output bridle roll. The electromagnetic ultrasonic wave device comprises a transmitting amplifier 3, a resonant electromagnetic ultrasonic wave sensor 4, a receiving amplifier 7, a gate 8 and a frequency analyzer 9. The principal part of the computing device comprises a computer 2, and the computer 2 provides instructions for setting measuring conditions and instructions for a measurement to the frequency analyzer 9 to control the frequency analyzer 9. Further, the computer 2 has a function of controlling the timing of transmission of the transmitting amplifier 3 and, at the same time, has a function of controlling the timing of receiving of the receiving amplifier. Further, the computer 2 has a function of receiving data of analytical results obtained from the frequency analyzer and a function of calculating the Young's modulus and Lankford value through the computation of the thickness resonant frequency ratios, $K_1$ and $K_2$, wherein use is made of these data. The controlling device 5 has a controlling mechanism for maintaining a constant gap between the resonant electromagnetic ultrasonic wave sensor 4 and the cold rolled thin steel sheet 6 and conducting lifting and shunting. Specifically, the controlling device 5 has a function of conducting an adjustment when the thickness of the cold rolled thin steel sheet varies in such a manner that the gap becomes constant, and maintaining the gap at a constant value while measuring the gap when the cold-rolled thin steel sheet 6 oscillates. Further, the computer 2 has a function of providing an instruction for change in the sheet thickness to the controlling device 5. The bridle rolls 10 and 11 have a function of suppressing the occurrence of vibration (fluttering) of the cold-rolled thin steel sheet 6. In this case, it is unnecessary to provide the resonant electromagnetic ultrasonic wave sensor 4 at the positions of the bridle rolls 10 and 11, and the sensor may be provided in a mechanism for suppressing the fluttering of the cold rolled thin steel sheet 6.

A solid line in FIG. 7 represents a flow of a signal or information, and a broken line represents a flow of control.

In FIG. 7, when the Young's modulus and Lankford value of a cold rolled thin steel sheet are computed, a high frequency burst current is fed to the coil while sweeping a frequency from the frequency analyzer 9, and the output high frequency current is amplified by means of a transmitting amplifier 3. The high frequency current output from the transmitting amplifier 3 flows into the resonant electromagnetic ultrasonic wave sensor 4, and as a result, interaction between the high frequency current and the previously applied magnetic field leads to the generation of two transverse ultrasonic waves and one longitudinal ultrasonic wave in the cold rolled thin steel sheet 6. These three ultrasonic waves are detected by means of the resonant electromagnetic sensor 4, amplified by means of a receiving amplifier 7, and input into a gate 8. In the gate 8, the thus detected signal is taken out in a timing delayed by a predetermined time with respect to the timing of the transmission of the transmitting amplifier 3. A signal having the same frequency component as the high frequency current output from the frequency analyzer 9 is extracted by means of the frequency analyzer 9 from signals taken out of the gate 8. Finally, the in-plane average value of Young's modulus and the in-plane average value of Lankford values are approximately obtained from two thickness resonant frequency ratios $K_1$ and $K_2$; the ratio value $K_3$ is regarded as a constant value and the known values of a single crystal of iron are $C^0_{11}$, $C^0_{12}$ and $C^0_{44}$.

Figure 8:
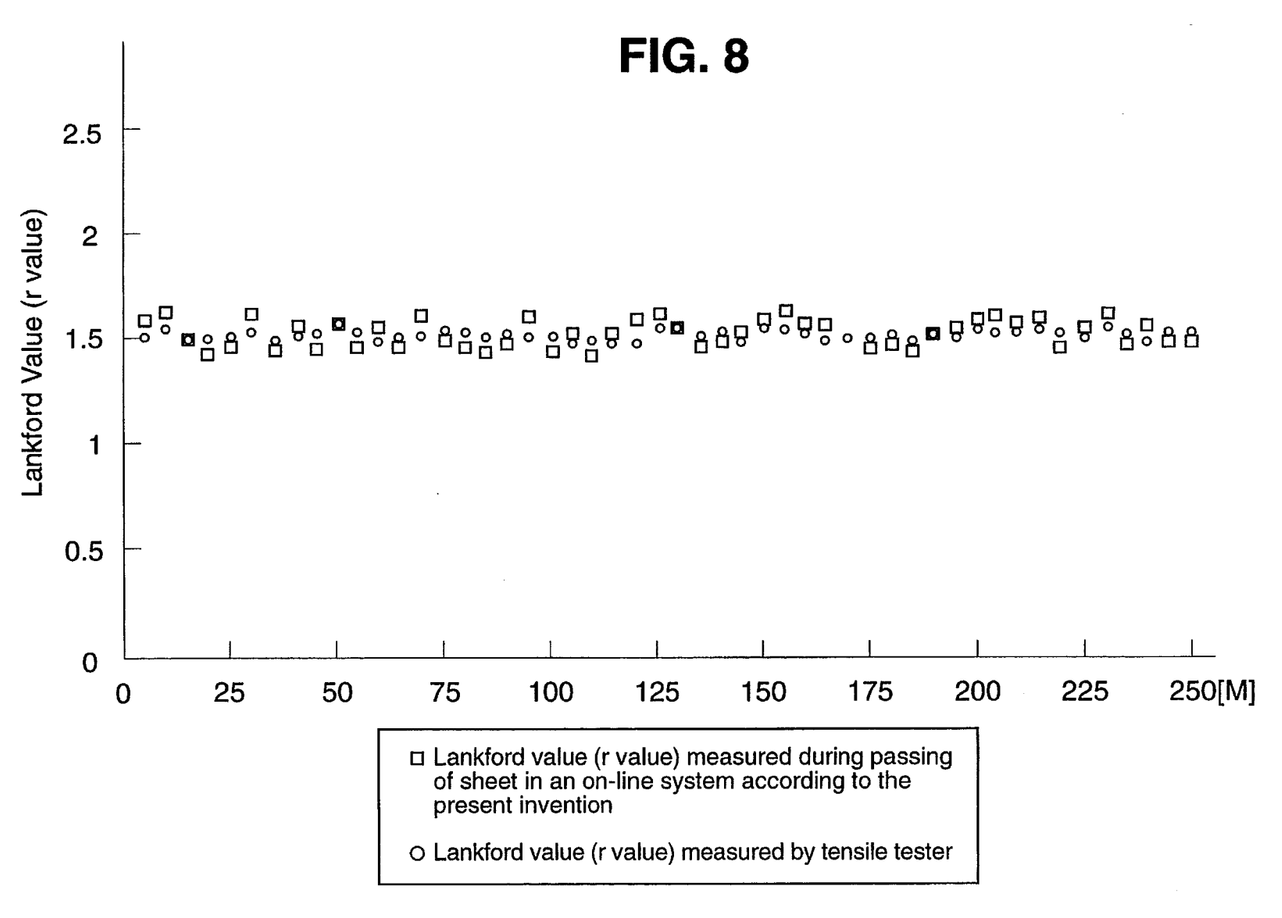
FIG. 8 is a diagram showing the results of measurement of Lankford value (r value) of a cold rolled thin steel sheet when passing through an on-line system.

FIG. 8 is a diagram showing the results of a measurement of the Lankford value of the cold rolled thin steel sheet during the passing of a steel sheet in an on-line system. Specifically, the results of the measurement of the in-rolling-plane average value of Lankford value (r value) of the cold rolled thin steel sheet at intervals of 5 m during the passing of the steel sheet in an on-line system are shown in FIG. 8. The results of a measurement according to the method of the present invention are indicated by □, and the results of a measurement by means of a tensile tester after cutting the cold rolled steel sheet are indicated by ○. As is apparent from FIG. 8, although the range of the Lankford value is narrow, the results of a measurement according to the present invention are in agreement with the values measured by the tensile tester.

In the present invention, it is possible to obtain the in-plane average value of Young's modulus or the in-plane average value of Lankford value according to an approximate computation formula through the utilization of resonant frequency ratios, $K_1$ and $K_2$, by making use of a resonant electromagnetic ultrasonic wave sensor in a completely non-destructive manner without staining the cold rolled thin steel sheet. In an off-line system, it is possible to simply and rapidly measure the in-plane average value of Young's moduli or the in-plane average value of Lankford values. With the present invention it becomes possible to measure the in-plane average value of Young's moduli or the in-plane average value of Lankford values of the cold rolled thin steel sheet even during the passing of the steel sheet in an on-line system, which renders the measuring method and measuring apparatus of the present invention useful for quality control in an on-line system.

We claim:

1. A method for measuring properties of a cold rolled thin steel sheet wherein said cold rolled thin steel sheet has a rolling direction and a thickness, with the thickness having a direction perpendicular to the rolling direction, said method comprising:

determining, as a first thickness resonant frequency, a resonant frequency of a first transverse ultrasonic wave propagating within the cold rolled thin steel sheet in the thickness direction, said first transverse ultrasonic wave being polarized in a direction parallel to the rolling direction;

determining, as a second thickness resonant frequency, a resonant frequency of a first longitudinal ultrasonic wave propagating within the cold rolled thin steel sheet in the thickness direction;

determining, as a first ratio, a ratio of said first thickness resonant frequency to said second thickness resonant frequency;

determining, as a third thickness resonant frequency, a resonant frequency of a second transverse ultrasonic wave propagating within the cold rolled thin steel sheet in the thickness direction, said second transverse ultrasonic wave being polarized in a direction normal to the rolling direction;

determining, as a second ratio, a ratio of said third thickness resonant frequency to said second thickness resonant frequency;

regarding as a constant value a third ratio, said third ratio being a ratio of a SHO plate wave velocity propagating within the cold rolled thin steel sheet in a direction at 45° to the rolling direction to a SHO plate wave velocity propagating within the cold rolled thin steel sheet in a direction parallel to or normal to the rolling direction;

computing in-plane average value of Young's moduli and in plane average value of Lankford values of the cold rolled thin steel sheet from said three ratios and a known modulus of elasticity of a single crystal of iron.

2. A method for measuring properties of a cold rolled thin steel sheet according to claim 1, wherein said first and second transverse ultrasonic waves and said longitudinal ultrasonic wave are generated and detected by using at least one electromagnetic ultrasonic wave device having a resonant electromagnetic ultrasonic wave sensor to measure said thickness resonant frequency ratio.

3. A method for measuring properties of a cold rolled thin steel sheet according to claim 2, wherein said electromagnetic ultrasonic wave device comprises a coil for conducting a current for inducing an eddy current in the cold rolled thin steel sheet, a magnet for applying a predetermined magnetic field in the cold rolled thin steel sheet and said resonant ultrasonic wave sensor for detecting said first and second transverse ultrasonic waves and said longitudinal ultrasonic wave generated in the vicinity of the surface of the cold rolled thin steel sheet owing to mutual action between the eddy current and the magnetic field, and the thickness resonant frequencies are determined by generating and detecting the the first and second transverse ultrasonic waves and longitudinal ultrasonic waves while sweeping the frequency of a current flowing in said coil and recording a frequency at which the detected ultrasonic wave becomes maximum.

4. An apparatus for measuring properties of a cold rolled thin steel sheet, said apparatus including:

at least one electromagnetic ultrasonic wave device having a resonant electromagnetic wave sensor to measure thickness resonant frequency ratios, said cold rolled thin steel sheet having a rolling direction and a thickness with the thickness having a direction perpendicular to the rolling direction;

means for measuring, as a first, thickness resonant frequency, a resonant frequency of a first transverse ultrasonic wave propagating within the cold rolled thin steel sheet in the thickness direction, said first transverse ultrasonic wave being polarized in a direction parallel to the rolling direction;

means for measuring, as a second thickness resonant frequency, a resonant frequency of a longitudinal ultrasonic wave propagating within the cold rolled thin steel sheet in the thickness direction;

means for measuring, as a first ratio, a ratio of said first thickness resonant frequency to said second thickness resonant frequency;

means for measuring, as a third thickness resonant frequency, a resonant frequency of a second transverse ultrasonic wave propagating within the cold rolled thin steel sheet in the thickness direction, said second transverse ultrasonic wave being polarized in a direction normal to the rolling direction;

means for measuring, as a second ratio, a ratio of said third thickness resonant frequency to said second thickness resonant thickness frequency;

means for regarding as a constant value a third ratio, said third ratio being a ratio of a SHO plate wave velocity propagating within said cold rolled thin steel sheet in a direction at 45° to the rolling direction to a SHO plate wave velocity propagating within said cold rolled thin steel sheet in a direction parallel to or normal to the direction of rolling;

means for computing in-plane average value of Young's moduli and in-plane average value of Lankford values of the cold rolled thin steel sheet from said three ratios and from a known modulus of elasticity of a single crystal of iron.

5. An apparatus for measuring properties of a cold rolled thin steel sheet according to claim 4 which further includes means for controlling a gap between the resonant electromagnetic ultrasonic wave sensor and the cold rolled thin steel sheet at a constant value.

\* \* \* \* \*